(12) United States Patent
Gwy et al.

(10) Patent No.: US 6,653,095 B1
(45) Date of Patent: Nov. 25, 2003

(54) HYDROGEN PEROXIDE MONITORING

(76) Inventors: Alan Gwy, 43 Station Road, Llanishen Cardiff CF4 5UT (GB); Philip Jeffrey Cunnah, 70 The Parade, Pontypridd CF37 4PY (GB); Freda Hawkes, 29 Nant Fawr Road, Cyn-Coed, Cardiff CF23 6JQ (GB); Dennis Hawkes, 29 Nawt Fawr Road, Cyn-Coed, Cardiff CF23 6JQ (GB); Richard Dinsdale, Town Foot Farm, Carlton, Leyburn, North Yorks DL8 4LB (GB)

( * ) Notice: Subject to any disclaimer, the term of this patent is extended or adjusted under 35 U.S.C. 154(b) by 11 days.

(21) Appl. No.: 10/049,190

(22) PCT Filed: Aug. 14, 2000

(86) PCT No.: PCT/GB00/03124

§ 371 (c)(1),
(2), (4) Date: Apr. 12, 2002

(87) PCT Pub. No.: WO01/12843

PCT Pub. Date: Feb. 22, 2001

(30) Foreign Application Priority Data

Aug. 12, 1999 (GB) ................................................ 9918945

(51) Int. Cl.[7] .............................. C12Q 1/30; C12Q 1/28; C12Q 1/26; C12Q 1/00; C12M 1/34
(52) U.S. Cl. ............................ 435/27; 435/28; 435/25; 435/4; 435/283.1; 435/287.1; 435/287.5
(58) Field of Search ............................ 435/27, 28, 25, 435/4, 283.1, 287.1, 287.5

(56) References Cited

U.S. PATENT DOCUMENTS

| | | | |
|---|---|---|---|
| 3,926,732 A | 12/1975 | Rosen et al. | 195/103.5 |
| 4,153,510 A | 5/1979 | Messing et al. | 195/59 |
| 4,202,938 A | 5/1980 | Haeckel et al. | 435/10 |
| 4,338,399 A | 7/1982 | Weil et al. | 435/99 |
| 4,356,092 A | 10/1982 | Shimizu et al. | 435/262 |
| 4,414,334 A | 11/1983 | Hitzman | 435/262 |
| 4,460,686 A * | 7/1984 | Hartmeier | 435/137 |
| 4,663,044 A | 5/1987 | Goronszy | 210/610 |
| 4,765,901 A | 8/1988 | Field | 210/603 |
| 5,098,830 A | 3/1992 | Bar-or et al. | 435/28 |
| 5,863,749 A * | 1/1999 | Hawkes et al. | 435/28 |
| 5,972,637 A * | 10/1999 | Hawkes et al. | 435/28 |

FOREIGN PATENT DOCUMENTS

| | | |
|---|---|---|
| EP | 0 053 865 | 6/1982 |
| EP | 0 181 210 | 5/1986 |
| GB | 2 273 773 A | 6/1994 |

OTHER PUBLICATIONS

A.J. Guwy et al.; "Active Biomass in Activated Sludge: Comparison of Respirometry With Catalase Activity Measuring Using An On–Line Monitor"; Water Research, NL, Elsevier Science Publishers, Amsterdam, vol. 32, No. 12; Dec. 1, 1998; p. 3706.

(List continued on next page.)

Primary Examiner—Louise N. Leary
(74) Attorney, Agent, or Firm—Vinson & Elkins L.L.P.

(57) ABSTRACT

A method and apparatus for determining the hydrogen peroxide content of a fluid. The method includes: (a) contacting the fluid with a catalyst so as to permit decomposition of the hydrogen peroxide present in the fluid to oxygen and water; permitting the oxygen liberated to pass to gas meter; and (c) measuring the volume of oxygen liberated utilizing the gas meter, wherein the volume of oxygen liberated provides a measure of the hydrogen peroxide content of the fluid.

17 Claims, 5 Drawing Sheets

OTHER PUBLICATIONS

A. J. Guwy et al.; "A Technique For Monitoring Hydrogen Peroxide Concentration Off–line and On–line"; Water Research, NL, Elsevier Science Publishers, Amsterdam, vol. 34, No. 8; Jun. 2000; pp. 2191–2198.

International Publication No. WO 98/30884, international publication date of Jul. 16, 1998, of international filing date: Dec. 23, 1997; Gerdt Fladda et al., "Method And Arrangement For Measuring The Content Of Chemicals During Bleaching."

E. Vock–Gassmann et al.; "Control of Oxygen Content with 02 Sensors During Fermentation of Biomass"; Chemical Abstracts, vol. 118, No. 3; Jan. 18, 1993; p. 575.

D. Siegmund et al.; "Estimation of Fermentation Biomass Concentration by Measuring Oxygen Uptake Off–Line with an Oxygen Electrode"; Chemical Abstracts, vol. 112, No. 7; Feb. 12, 1990, p. 579.

International Publication No. WO 96/18896, international publication date of Jun. 20, 1996, of international filing date: Dec. 18, 1995; Dennis Hawkes, et al., "Determining The Organic Content Of A Fluid".

International Search Report—PCT/GB95–02949 dated Feb. 21, 1996.

* cited by examiner

HYDROGEN PEROXIDE MONITORING

TECHNICAL FIELD OF THE INVENTION

The application is a national stage entry of PCT/GB00/03124, filing date Aug. 14, 2000.

The present invention is concerned with a method of monitoring the content of peroxide present in a fluid sample, and apparatus for such a method.

BACKGROUND OF THE INVENTION

Hydrogen peroxide has been used as an oxidant in industrial applications for many years. Hydrogen peroxide is, for example, a stronger oxidant than chlorine or permanganate and has the advantage of non-polluting decomposition products.

Hydroxyl radicals (OH•) are highly oxidising species. The most commonly accepted mechanism for hydroxyl radical production is the photolysis of hydrogen peroxide. Photochemical reduction of $Fe^{3+}$ to $Fe^{2+}$ (UV/Fentons) in the presence of hydrogen peroxide, increases the generation of OH• radicals and may yield a more effective system for oxidative degradation.

A major application of peroxide is in advanced oxidation processes removing recalcitrant organic contaminants, such as herbicides and PCB's (polychlorinated biphenyls). For example, the purification of water containing organic impurities by peroxide (approx 1%)/UV treatment has been used since the early 1980's. In addition, peroxide together with UV and $O_3$, has been used at a field scale to treat ground water contaminated with volatile organic compounds.

The partial oxidation of recalcitrant compounds may also be advantageous. It has been shown by Carberry and Benzing (Water Sci. Tech 23, 1991, 367–376) that two chlorinated aromatics showed enhanced biodegradability after pre-oxidation with peroxide at molar ratios between 2:1 and 6:1, with an optimum at 4:1.

The use of hydrogen peroxide as an oxidant has several advantages over other methods of chemical and photochemical water treatments, namely its thermal stability, the ability to store on-site, its solubility in water, and the lack of mass transfer problems of associated gases.

Peroxides are used in the removal of color, especially as a bleaching agent in the textile industry. In addition, peroxides are used in the manufacture of paper, and during waste paper recycling.

Other environmental applications include the oxidation of sulfides for odor control, corrosion control of waste pipes by addition of hydrogen peroxide to waste water, an additional oxygen source for overloaded activated sludge plants and controlling filamentous bulking.

It can be seen from the above that the use of hydrogen peroxide in industry has numerous advantages. However, the concentration of peroxide employed in the industrial processes must be carefully controlled and monitored for its efficient and cost effective usage.

There are many methods of monitoring hydrogen peroxide known in the art. Standard methods of monitoring hydrogen peroxide include titrimetric (typically based on the oxidation of hydrogen peroxide with permanganate, followed by the reduction with acidic potassium iodide), gasometric, electrochemical calorimetric, chemiluminescent and acoustic methods. The results of these monitoring methods can then be used to control the process.

The methods outlined above can be time consuming, sensitive to interference, and have poor lifetime. They may not be so effective for process monitoring and control.

PCT patent specification WO98/30884 to BTG Källe Inventing AB (BTG) discloses a method and device for measuring the content of chemicals (such as hydrogen peroxide) used in connection with bleaching of cellulose fibres. The method includes adding the enzyme catalase to the sample, which is agitated so as to permit the hydrogen peroxide to decompose and oxygen gas to be generated. The resultant oxygen gas pushes out a certain sample volume for the measurement of the sample; the sample volume is then, directly or indirectly, converted to a value representing the amount of hydrogen peroxide present.

In addition, the above mentioned patent specification suggests that it is not possible to measure directly the volume of oxygen produced.

SUMMARY OF THE INVENTION

These and other needs in the art are addressed by a method of determining the hydrogen peroxide content of a fluid, which method includes;

(a) contacting the fluid with a catalyst so as to permit decomposition of the hydrogen peroxide present in the fluid to oxygen and water;

(b) permitting the oxygen liberated to pass to a gas meter; and (c) measuring the volume of oxygen liberated utilizing the gas meter, wherein the volume of oxygen liberated provides a measure of the hydrogen peroxide content of the fluid.

The term "fluid" is a term generally used in the art for any material which can be pumped. Non-limiting examples of such fluids are solutions, slurries, pulps, gravel, etc.

It is preferred that the gas meter is arranged to measure low and irregular gas flows with a low back pressure. Typically, the gas meter is a low flow gas meter, such as the meter described in "On-line low flow high precision gas metering systems", Wat. Res, vol 29, page 977–979 (1995), the disclosure of which is incorporated by reference.

The volume may be measured as an absolute volume, or as a rate of evolution (in other words, the volume evolved in a unit time).

It is preferred that the volume of oxygen liberated in step (b) is measured directly.

It is preferred that the catalyst is an enzyme, such as catalase, which may be either soluble or immobilised. However other suitable catalysts may be used. Preferably, the catalase is Hydrogen peroxide: hydrogen peroxide oxidoreductase, EC 1.11.1.6. The catalase catalyses the decomposition of hydrogen peroxide to water and oxygen gas.

Typically, the amount of catalase present in step (a) is predetermined. It is also preferred that the catalase is present in an amount excess relative to the hydrogen peroxide.

It is preferred that the mixing and catalysed release of oxygen in step (a) is carried out for sufficient time to decompose substantially all of the hydrogen peroxide present in the fluid.

The temperature of the process may be kept at a predetermined temperature, for example, in the range from 20° C. to 40° C.

Preferably, the oxygen liberated may be measured using a pressure transducer or the like, such as a low-flow gas meter. Thus, the hydrogen peroxide content of the sample at any given time may be determined, for example, in a continuous treatment process.

Preferably, the measurements by the gas meter of the oxygen liberated from the sample are passed to a data acquisition system for processing, where, advantageously, the information may be calibrated to produce an accurate reading of the hydrogen peroxide present in the sample.

Advantageously, when it is required to measure small amounts of hydrogen peroxide, such as about 25–500 mg.l$^{-1}$, the fluid sample is aerated prior to contacting with the catalyst.

The method according to the invention may be used in a wide range of industrial applications, for example, in paper processing, textile processes, steel industry and water treatment.

According to a second aspect of the present invention, there is provided apparatus for determining the hydrogen peroxide content of a fluid, which apparatus includes:

(a) a first receptacle arranged to (i) receive the fluid and a catalyst, and (ii) to permit decomposition of the hydrogen peroxide present to oxygen and water;

(b) a gas meter arranged to measure the oxygen evolved.

It is preferred that the flow of fluid and the catalyst are controlled using at least one suitable peristaltic pump and/or at least one centrifugal pump.

In a first embodiment of the second aspect of the present invention, the apparatus is suitable for use in continuous measurements. In this embodiment, the fluid in the receptacle is maintained at a volume of about 15–60 cm$^3$, preferably about 50 cm$^3$. The volume may be advantageously controlled using a manometer.

The apparatus preferably includes aeration means when it is required to measure small amounts of hydrogen peroxide, such as about 25–500 mg.l$^{-1}$.

In a second embodiment of the second aspect of the present invention, the apparatus is suitable for use in batch measurements. In this embodiment, the fluid in the receptacle is maintained at about 25–2000 cm$^3$, preferably about 1000 cm$^3$.

According to a third embodiment of the present invention, there is provided a gas flow meter for use in the measurement of oxygen which is liberated as a result of the decomposition of hydrogen peroxide, the decomposition being a result of contacting the hydrogen peroxide with a catalyst.

It is preferred that the gas meter comprises a three way solenoid valve, a sensitive differential pressure transducer and a ballast chamber.

The pressure transducer is preferably based on a steel diaphragm which advantageously is not significantly affected by temperature changes and is resistant to corrosion by water-saturated gases. Preferably, the solenoid valve comprises a dry paddle solenoid valve, typically made from a material which is resistant to corrosive gases. Such a valve is advantageously corrosion resistant.

The output from the differential pressure transducer may, in some embodiments, be smoothed, typically by an RC circuit or other conventional methods.

It is therefore an aim of the present invention to provide a rapid method to monitor hydrogen peroxide over a wide range of concentrations.

It is a further aim of the present invention to provide a method for on-line monitoring of hydrogen peroxide which utilizes direct measurement of the oxygen gas produced in the decomposition of hydrogen peroxide.

It is yet a further aim of the present invention to provide a monitor which is capable of monitoring hydrogen peroxide in "dirty" and "high solid content" environments such as industrial process streams and effluents without fouling or interference which is one of the major drawbacks of currently available instruments.

DETAILED DESCRIPTION OF THE INVENTION

Figure 1:
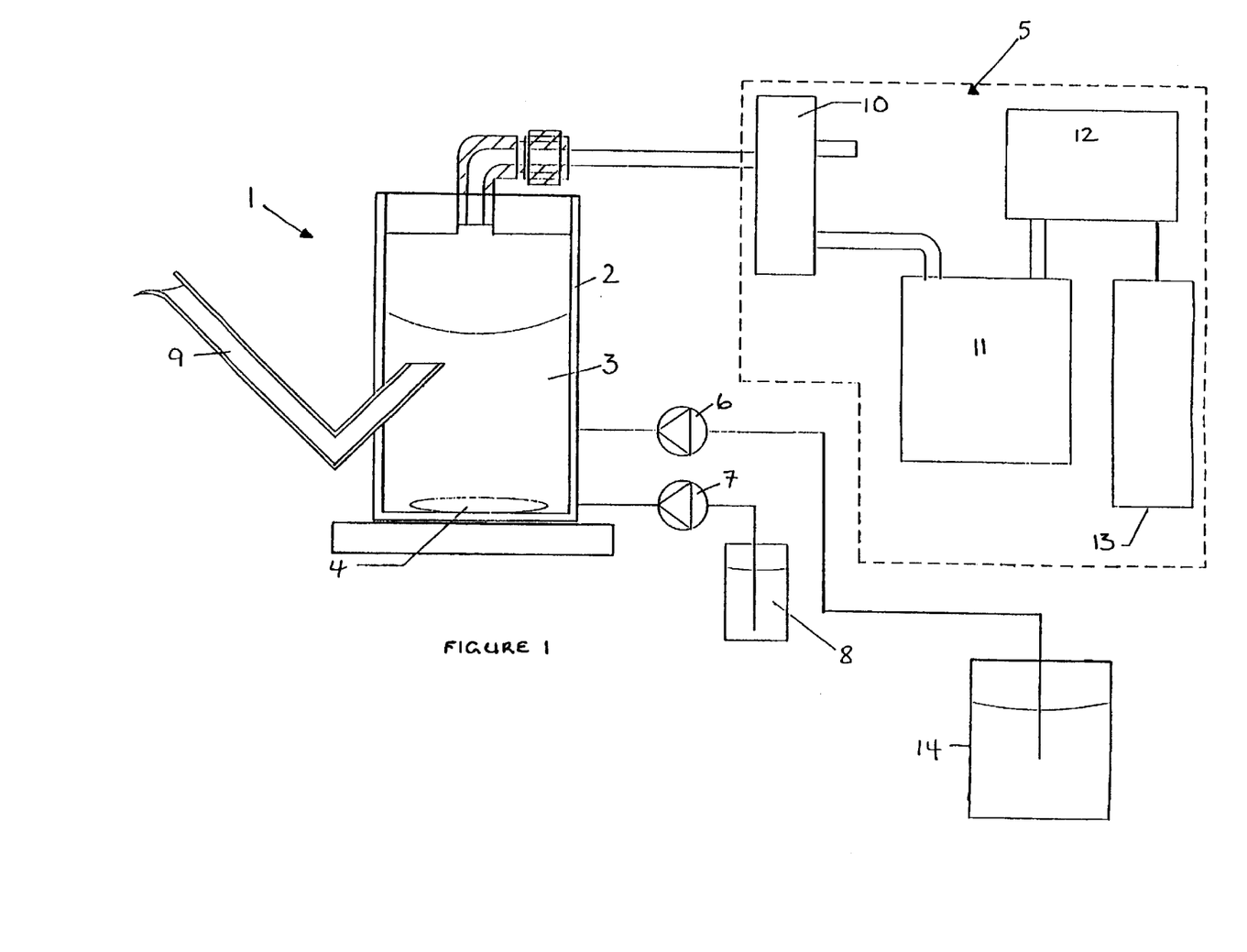
FIG. 1 represents an embodiment of apparatus according to the present invention for measurement of hydrogen peroxide.

The present invention will now be illustrated, by way of example only, with reference to FIG. 1 of the accompanying drawings, which represents an embodiment of apparatus according to the present invention for measurement of hydrogen peroxide.

Standard hydrogen peroxide solutions were prepared from a 30% solution. The catalase, commercially available from Biocatalysts Limited, UK was produced from a selected strain of *Aspergillus niger* (this catalase is heat stable, active in a broad pH range and less susceptible to the deactivating effects of hydrogen peroxide when compared with bovine sources). Various dilutions of the catalase supplied was used in the experiments outlined below:

Continuous Experiments

Referring to FIG. 1, the continuous experiments were carried out in a hydrogen peroxide monitor 1 consisting of an acrylic reaction chamber 2 (26 cm$^3$ total volume), with a working liquid volume 3 of 17 cm$^3$ (the working liquid volume 3 is maintained at 17 cm$^3$ by manometer 9); the contents were mixed by a magnetic stirrer bar 4. The chamber was housed in a SI 60 D variable temperature controlled incubator (Stuart Scientific Co. UK) supplied by Fisher Scientific UK (not shown). The chamber was connected to a LFM100 gas meter (G H Zeal Ltd).

The gas meter 5 comprises a solenoid valve 10, a ballast chamber 11, a sensitive pressure transducer 12 and a control circuit and acquisition system 13. Data from the monitor was logged on a PC with a interface card (DAQ 700) using LabVIEW (a trade mark of National Instruments, Newbury, UK). The Virtual instrument (VI) was configured to sample the output from the monitor at 1 minute intervals and download to "Microsoft Excel" (both being trade marks) for off-line processing.

Figure 2:
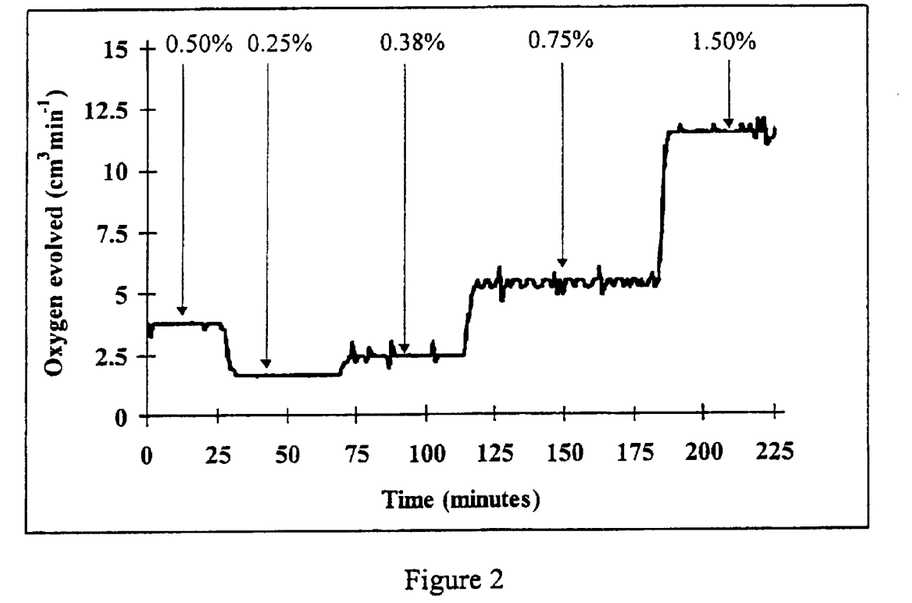
FIG. 2 is a graph of the oxygen produced from hydrogen peroxide standards using a continuous operated hydrogen peroxide monitoring method.
Figure 3:
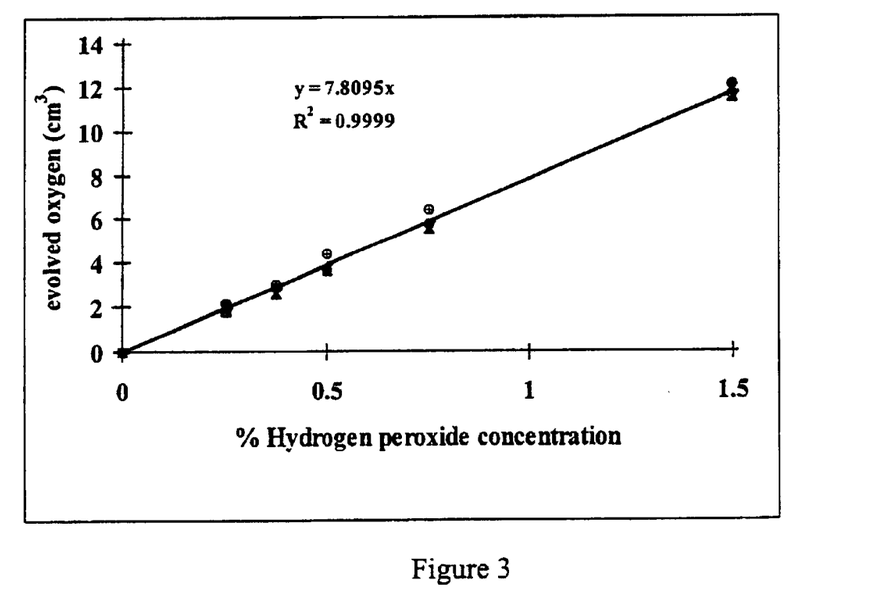
FIG. 3 is a graph representing the correlation of oxygen produced against peroxide standards using a continuous operated hydrogen peroxide monitoring method.

The standard hydrogen peroxide 14 was introduced into reaction chamber 2 using a 505 $\mu$ peristaltic pump 6 (Watson-Marlow Ltd, Poole, UK) with an 8-roller multi-channel pump head at a rate of 2.2 cm$^3$ min$^{-1}$. Similarly, the 1% catalase solution 8 was introduced into reaction chamber 2 using a 505 $\mu$ peristaltic pump 7 (Watson-Marlow Ltd, Poole, UK) with an 8-roller multi-channel pump head at a rate of 0.075 cm$^3$ min$^{-1}$. Duplicate runs of each hydrogen peroxide solution were performed at three different temperatures of 30, 25 and 45° C. The oxygen production rate for each run was calculated as the average of at least 25 minutes of steady state gas production. FIGS. 2 and 3 show examples of results obtained for measurements carried out in these experiments.

Experiments in Batch Mode

In one set of experiments the hydrogen peroxide monitor was similar in construction to that depicted in FIG. 1. It consisted of an acrylic reaction chamber having 70 cm$^3$ total volume. The liquid temperature was controlled using a water jacket and a Grant FH15 (Cambridge, UK) flow heater. The chamber was connected to a LFM100 gas meter (G H Zeal Ltd, UK). Data from the monitor was logged on a PC with an interface card (DAQ 700) using LabVIEW (a trade mark of National Instruments, Newbury, UK). The Virtual instrument was configured to sample the output from the monitor at 1 minute intervals and download to "Microsoft Excel" (both trade marks) for off line processing.

Figure 4:
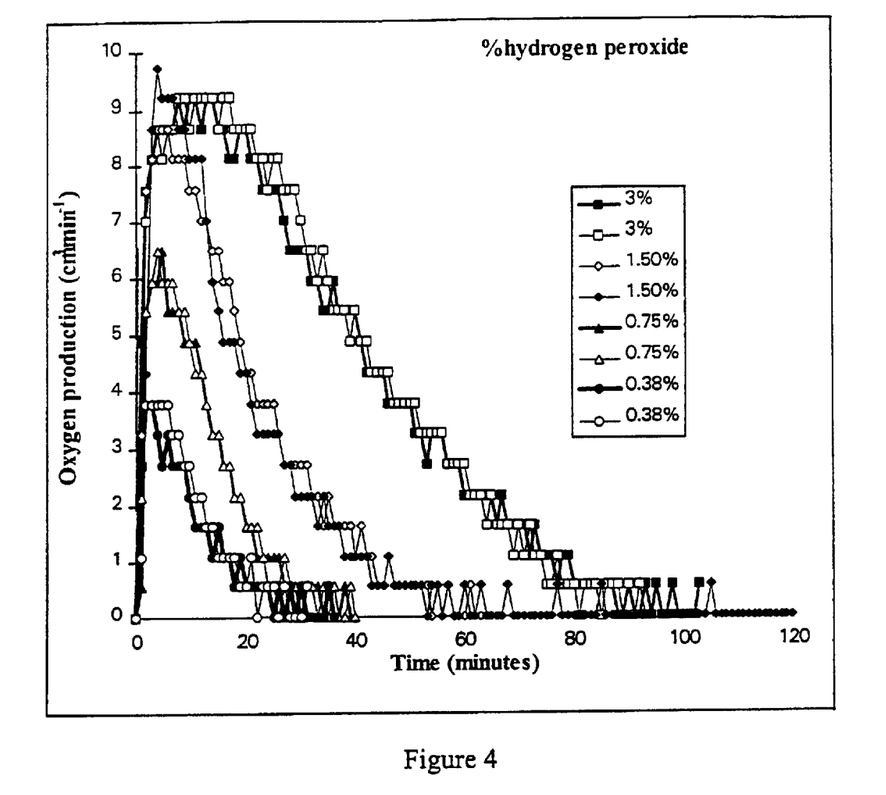
FIG. 4 is a graph of the oxygen produced from hydrogen peroxide standards using a batch operated hydrogen peroxide monitoring method.
Figure 5:
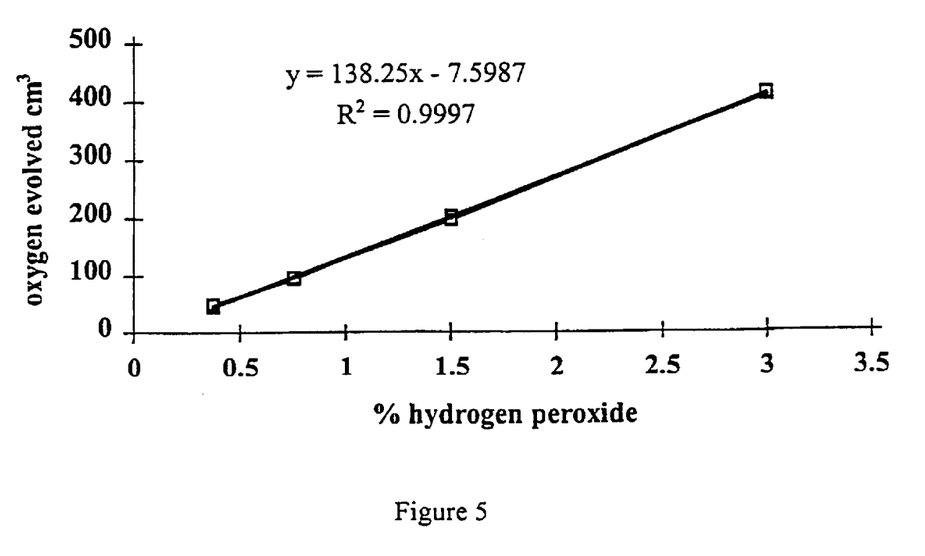
FIG. 5 is a graph representing the correlation of oxygen produced against hydrogen peroxide standards using a batch operated hydrogen peroxide monitoring method.

A 25 cm$^3$ sample of hydrogen peroxide was pipetted into the chamber, which was then sealed. A 1% solution of the catalase was then pumped into reaction chamber using a 505 $\mu$ peristaltic at a rate of 0.075 cm$^3$ min$^{-1}$ (Watson & Marlow Ltd., Poole, UK). The catalase was continuously pumped into the reaction chamber until all the hydrogen peroxide had completely degraded and gas evolution had ceased, the total oxygen production was than calculated taking into account the displacement caused by introduction of catalase. Duplicate runs of each hydrogen peroxide solution were performed at 25° C. FIGS. 4 and 5 show examples of results of experiments carried out with this monitor measuring from 0.25 to 1.5% hydrogen peroxide solutions in sodium dihydrogen orthophosphate buffer at pH7.

In a further set of experiments, the hydrogen peroxide monitor consisted of an acrylic chamber with a working volume of 1 litre. The reaction chamber was located in a temperature controlled enclosure to maintain the temperature of the reaction. The contents of the reaction chamber were mixed by recirculation of the reactor contents by means of a centrifugal pump. The reaction chamber was connected to a low flow gas meter, the technology as described previously. A data logger recorded output from the gas flow meter at predefined intervals and this was downloaded via an RS232 port using "Easy Log" software onto a PC where the data was processed off-line using "Microsoft Excel", both being trade marks.

For measurement, the chamber was filled with pre-aerated sample to the predefined volume. The chamber was then sealed shut. A known volume of catalase reagent was then added. The gas flow due to injection of the reagent is known and compensated for. As catalyst was injected, a compensating volume was removed from the reaction chamber. The reaction was allowed to continue until all oxygen evolved was measured. The oxygen evolved passed to the gas flow meter where its passage through the meter was registered electronically in the data logger as a voltage. The hydrogen peroxide concentration could be calculated and was proportional to the total measured evolved oxygen registered as a cumulative voltage. The following equation can be used to determine the volume of oxygen based on the voltage measurement.

1 mol $O_2$=25.41L (273.15 K,0° C.)

1 mol $O_2$=25.29L (308.15 K,37° C.)[$p*V=n*R*T$; $V_1/V_2=T_1/T_2$]

1 mol $H_2O_2$=0.5 mole $O_2$=12.645 L 1 mL $O_2$=0.1 V

C=reaction volume in litres $$\text{1mg/L* (34.01 mg/mmol)}^{-1}*12.65 \text{ mL/mmol}*0.1 \text{ V/mL*C=1ppm} \\ H_2O_2 \Leftrightarrow y[\text{ppm } H_2O_2]=0.037 \text{ V/L*C} \quad \text{Equation:}$$

The chamber was emptied before repeating the process. Duplicate runs were performed using hydrogen peroxide solutions with the reaction chamber incubated at 37° C. FIGS. 6 to 9 show examples of results of various experiments carried out with this monitor for concentrations of peroxide between 0–300 ppm in solutions of water, (FIGS. 6 and 7), paper pulp filtrates filtered through a 500 $\mu$m mesh adjusted to pH10 using NaOH, (FIG. 8) and samples in water using different concentrations of catalase reagent, 1, 5 and 10%, (FIG. 9).

Results

The results of the experiments outlined above are given in the accompanying figures, wherein:

FIG. 2 is a graph of the oxygen produced from hydrogen peroxide standards using a continuous operated hydrogen peroxide monitoring method;

FIG. 3 is a graph representing the correlation of oxygen produced against peroxide standards using a continuous operated hydrogen peroxide monitoring method;

FIG. 4 is a graph of the oxygen produced from hydrogen peroxide standards using a batch operated hydrogen peroxide monitoring method; and FIG. 5 is a graph representing the correlation of oxygen produced against hydrogen peroxide standards using a batch operated hydrogen peroxide monitoring method.

Figure 6:
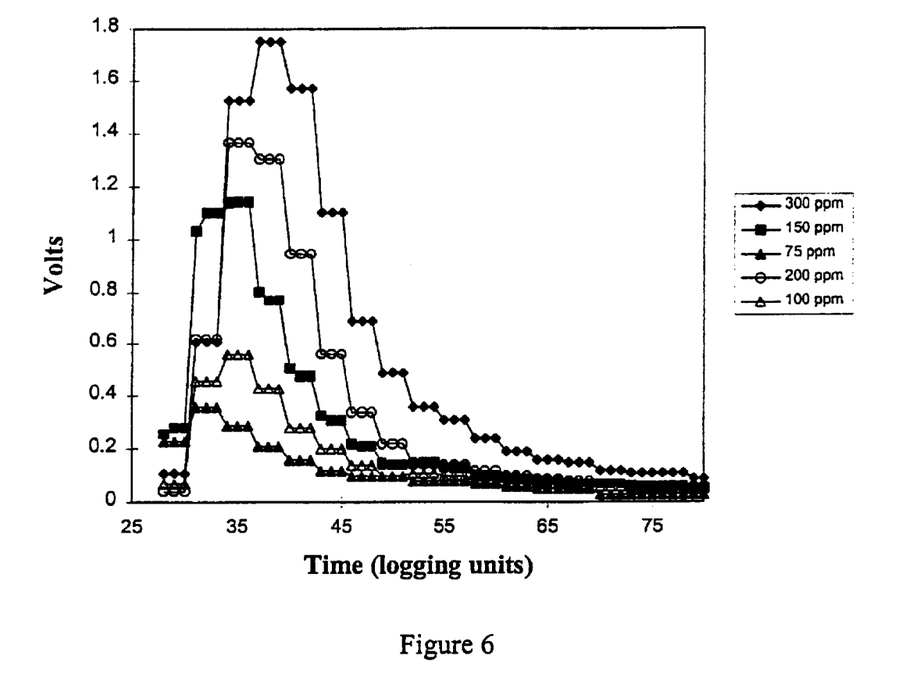
FIG. 6 shows oxygen evolution profiles for concentrations of hydrogen peroxide of 75, 100, 150, 200 and 300 ppm in water obtained by dosing of 10% catalase using a batch operated peroxide monitoring method.
Figure 7:
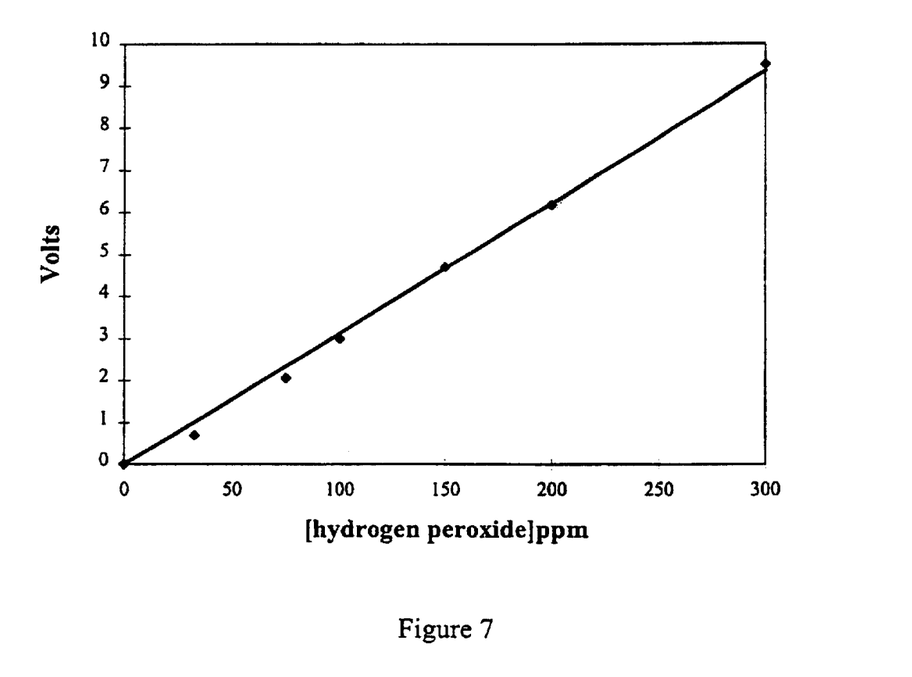
FIG. 7 shows the correlation of oxygen evolved against samples of known peroxide concentration in water from 0–300 ppm obtained by dosing of 10% catalase using a batch operated peroxide monitoring method.
Figure 8:
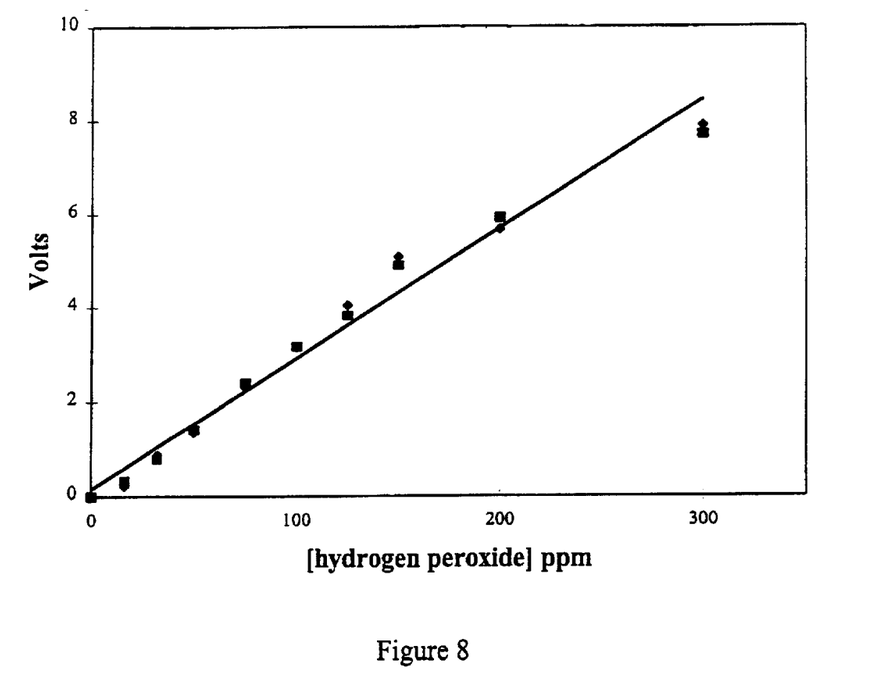
FIG. 8 shows the correlation of oxygen evolved against samples of known peroxide concentration (0–300 ppm) prepared from paper pulp filtrates, pH adjusted to 10, obtained by dosing of 10% catalase using a batch operated peroxide monitoring method.
Figure 9:
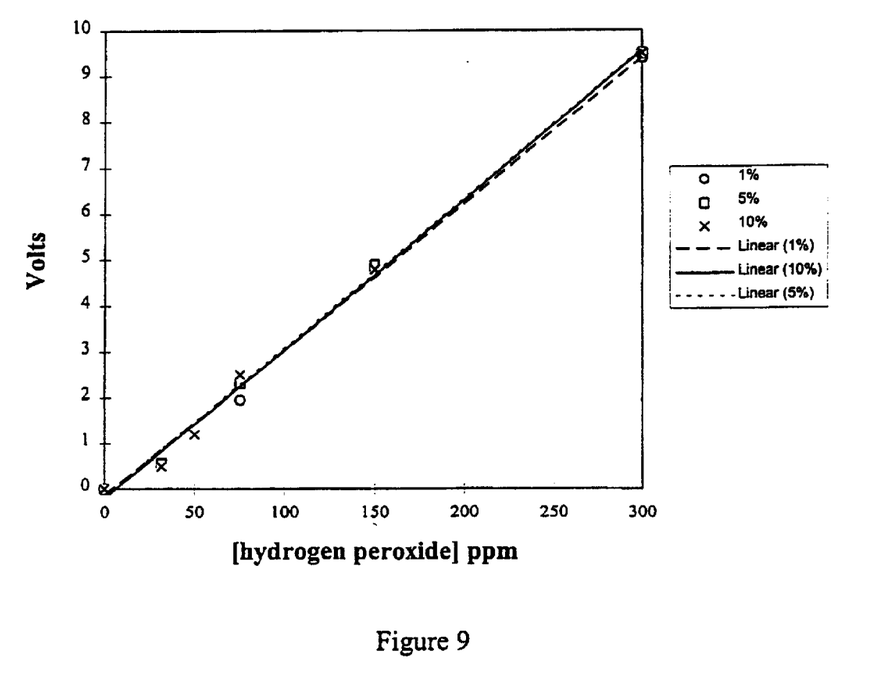
FIG. 9 shows the correlation of oxygen evolved for samples of known peroxide concentration in water (0–300 ppm) with dosing of different concentrations of catalase reagent into the chamber, 1,5 and 10%, using a batch operated peroxide monitoring method.

FIG. 6 shows oxygen evolution profiles for concentrations of hydrogen peroxide of 75, 100, 150, 200 and 300 ppm in water obtained by dosing of 10% catalase using a batch operated peroxide monitoring method;

FIG. 7 shows the correlation of oxygen evolved against samples of known peroxide concentration in water from 0–300 ppm obtained by dosing of 10% catalase using a batch operated peroxide monitoring method;

FIG. 8 shows the correlation of oxygen evolved against samples of known peroxide concentration (0–300 ppm) prepared from paper pulp filtrates, pH adjusted to 10, obtained by dosing of 10% catalase using a batch operated peroxide monitoring method;

FIG. 9 shows the correlation of oxygen evolved for samples of known peroxide concentration in water (0–300 ppm) with dosing of different concentrations of catalase reagent into the chamber, 1, 5 and 10%, using a batch operated peroxide monitoring method;

The method according to the invention may provide rapid measurement of peroxide in sample sizes of 20 ml or above. The method is more rapid than the existing titrimetric and colorimetric methods, and is not generally subject to interferences. The method can therefore also be used off-line to replace existing methods for peroxide determination both for industrial and research purposes.

We claim:

1. A method of determining the hydrogen peroxide content of a fluid, the method comprising:
   (a) aerating a sample of the fluid;
   (b) contacting the aerated sample with a catalyst so as to decompose the hydrogen peroxide present therein into oxygen and water;
   (c) passing the oxygen liberated in (b) through a gas meter; and
   (d) measuring the volume of oxygen liberated in (b) utilizing the gas meter,
wherein the volume of oxygen liberated provides a measure of the hydrogen peroxide content of the fluid.

2. The method according to claim 1, in which the gas meter is arranged to measure low and irregular gas flows with a low back pressure.

3. The method according to claim 1, in which the gas meter is a low flow gas meter.

4. The method according to claim 1, in which the volume of oxygen liberated in step (b) is measured directly.

5. The method according to claim 1, in which the catalyst is an enzyme.

6. The method according to claim 5, in which the enzyme is catalase.

7. The method according to claim 6, in which the catalase is hydrogen peroxide: hydrogen peroxide oxidoreductase, EC 1.11.1.6.

8. The method according to claim 1, in which the catalyst has at least one property selected from the group consisting of (1) soluble; and (2) immobilised.

9. The method according to claim 1, in which (b) includes contacting the aerated sample with a predetermined amount of catalyst.

10. The method according to claim 1, in which (b) is carried out for a sufficient time to decompose substantially all hydrogen peroxide present in the sample.

11. The method according to claim 1, in which the sample is maintained within a predetermined temperature range.

12. The method according to claim 11, in which the range is between about 20° C. and about 40° C.

13. A method according to claim 1, further comprising:
   (e) generating a parameter value representing the volume of oxygen measured in step (d); and
   (f) passing the parameter value to a data acquisition system.

14. A method of determining the hydrogen peroxide content of a fluid, the method comprising:
   (a) contacting a sample of the fluid with an enzyme catalyst so as to decompose the hydrogen peroxide present therein into to oxygen and water;
   (b) passing the oxygen liberated in (a) through a gas meter; and
   (c) measuring the volume of oxygen liberated in (a) utilizing the gas meter.

15. A system for determining the hydrogen peroxide content of a fluid, the system comprising:
   an aerator, the aerator disposed to aerate a sample of the fluid;
   a receptacle, the receptacle disposed to receive a catalyst and an aerated sample of the fluid, the receptacle further disposed host catalyzation of the aerated fluid sample by the catalyst wherein hydrogen peroxide within the aerated fluid sample decomposes into liberated oxygen and water; and
   a gas meter, the gas meter disposed to measure the volume of liberated oxygen.

16. The system according to claim 15, further comprising:
   at least one pump selected from the group, consisting of
      (a) a peristaltic pump; and
      (b) a centrifugal pump.

17. The system according to claim 15, further comprising:
   a manometer, the manometer disposed to maintain a predetermined volume of aerated fluid sample in the receptacle.

* * * * *